United States Patent
Lai et al.

(10) Patent No.: US 10,441,320 B2
(45) Date of Patent: Oct. 15, 2019

(54) SPINE CORRECTION APPARATUS

(71) Applicant: Chang Gung Memorial Hospital, Linkou, Taoyuan (TW)

(72) Inventors: Po-Liang Lai, Taoyuan (TW); Jaw-Lin Wang, Taoyuan (TW); Zong-Xing Chen, Taoyuan (TW)

(73) Assignee: CHANG GUNG MEMORIAL HOSPITAL, LINKOU, Taoyuan (TW)

( * ) Notice: Subject to any disclaimer, the term of this patent is extended or adjusted under 35 U.S.C. 154(b) by 0 days.

(21) Appl. No.: 15/456,616

(22) Filed: Mar. 13, 2017

(65) Prior Publication Data
US 2017/0265900 A1  Sep. 21, 2017

(30) Foreign Application Priority Data
Mar. 16, 2016 (TW) .............................. 105108084 A

(51) Int. Cl.
*A61B 17/70* (2006.01)
*A61B 17/00* (2006.01)

(52) U.S. Cl.
CPC .......... *A61B 17/705* (2013.01); *A61B 17/701* (2013.01); *A61B 17/7014* (2013.01); *A61B 2017/00477* (2013.01)

(58) Field of Classification Search
CPC ................ A61B 17/705; A61B 17/701; A61B 17/7014; A61B 2017/00477
USPC ....... 606/250, 251, 252, 258, 259, 260, 261, 606/264, 265, 278
See application file for complete search history.

(56) References Cited

U.S. PATENT DOCUMENTS

| | | | | |
|---|---|---|---|---|
| 6,264,658 B1* | 7/2001 | Lee | .................... | A61B 17/7002 606/252 |
| 7,029,472 B1* | 4/2006 | Fortin | ................ | A61B 17/7014 606/105 |
| 8,109,974 B2* | 2/2012 | Boomer | ............. | A61B 17/7013 606/256 |
| 8,956,392 B2* | 2/2015 | Khatchadourian | ......................... | A61B 17/7014 606/258 |
| 2006/0195088 A1* | 8/2006 | Sacher | ............... | A61B 17/7014 606/279 |
| 2009/0306717 A1* | 12/2009 | Kercher | ............. | A61B 17/7011 606/258 |
| 2013/0282064 A1* | 10/2013 | Arnin | ................. | A61B 17/7014 606/258 |
| 2015/0005824 A1* | 1/2015 | Arnin | ................. | A61B 17/7001 606/258 |

\* cited by examiner

*Primary Examiner* — Pedro Philogene
*Assistant Examiner* — David C Comstock
(74) *Attorney, Agent, or Firm* — Bacon & Thomas, PLLC

(57) ABSTRACT

A spine correction apparatus is disclosed, comprising: a first rod member having a first zone; a second rod member having a second zone; a first ring member having a first through-hole; and a second ring member having a second through-hole; wherein the first zone contacts the second zone, the first rod member and the second rod member are inserted into the first through-hole and the second through-hole, the first through-hole is fixed to the first rod member, and the second through-hole is fixed to the second rod member. The spine correction apparatus lowers the requirement for repeated surgeries and achieves the purpose of self-correction.

16 Claims, 14 Drawing Sheets

  
FIG. 2A  FIG. 2B  FIG. 2C
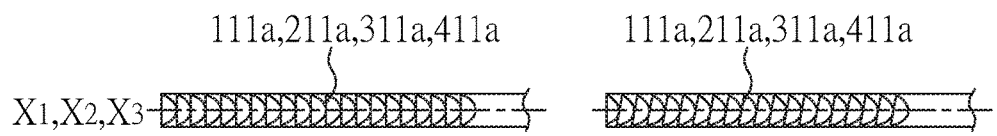
FIG. 3A  FIG. 3B
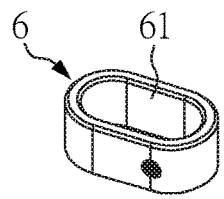 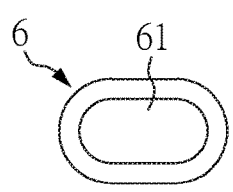 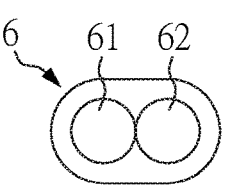 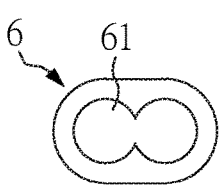
FIG. 4A  FIG. 4B  FIG. 4C  FIG. 4D
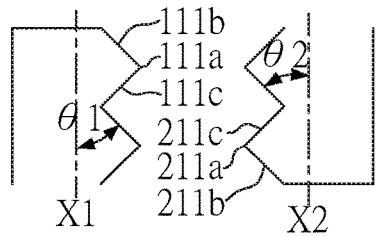
FIG. 5

SPINE CORRECTION APPARATUS

CROSS REFERENCE TO RELATED APPLICATION

This application claims the benefits of the Taiwan Patent Application Serial Number 105108084, filed on Mar. 16, 2016, the subject matter of which is incorporated herein by reference.

BACKGROUND OF THE INVENTION

1. Field of the Invention

The present invention relates to a spine correction apparatus, and more particularly to a spine correction apparatus for correction of scoliosis.

2. Description of Related Art

Scoliosis refers to an abnormal spinal deformity. The corrective spinal surgery needs to be performed for the patients who ineffectively respond to conservative treatment like bracing. Spinal fusion surgery is the most effective treatment to correct and control the Cobb angle of the deformity spine. But the spinal fusion surgery is not appropriate for the children whose spine is still growing, that will restrict their spinal growth, and lead to the impairment of pulmonary function and cardiac disease. The growing rod system is a non-fusion implant especially employed to correct the spinal deformity occurred in early onset scoliosis (EOS), at the same time, allow spine to growth.

The clinical used growing rod systems such as Pediatric ISOLA (DePuy Synthes Spine, Inc.) are effective in correcting and providing sufficient support to the deformity spines. However, these growing rod systems implanted into body needs to be extended by means of repeated surgeries as the children grow every 4 to 6 months. Patients receiving this treatment suffer from repeated surgeries is easy to have complications such as wound infection as well as the significant impact on their quality of life and psychological stresses. To reduce the need for repeated surgeries, some correction apparatuses featuring controlled-adjustment have been developed. Unfortunately, these known apparatuses are assembly complex and thus bulky. When implanted into human body, they tend to protrude out from skin surface or compress tissues or organs. While there are some apparatuses designed to be compact, they defectively have frangible axes. Other correction apparatuses like Luque trolley (DePuy Synthes Spine, Inc.) and Shilla (Medtronic International. Ltd.), which are both growth guidance systems that correct scoliosis by guiding spinal growth. However, their corrective effects are limited.

Given the shortcoming of the foregoing mentioned, there is a need for a correction apparatus capable of expanding with growth of one's spine, effectively correcting scoliosis, providing sufficient support to one's spine, and more importantly; saving the user from suffering repeated surgeries.

SUMMARY OF THE INVENTION

For addressing the foregoing need, the present invention provides a spine correction apparatus that delivers effective correction of scoliosis and sufficient spinal support, and eliminates the need of repeated surgeries for progressive adjustment, thereby significantly improving the effect of correction surgery and reducing patients' suffering.

The present invention provides a spine correction apparatus, comprising: a first rod having a first zone; a second rod having a second zone that is configured to contact the first zone; a first ring member having a first through-hole; and a second ring member having a second through-hole, wherein, the first rod and the second rod pass through the first through-hole of the first ring member and through the second through-hole of the second ring member, in which the first ring member is fixed to the first rod, and the second ring member is fixed to the second rod.

In the disclosed spine correction apparatus, the first zone has a plurality of first raised teeth, and the second zone has a plurality of second raised teeth, in which the first raised teeth and the second raised teeth are complementary and configured to engage with each other. Therein, each of the first raised teeth has a first top edge, a first lateral, and a second lateral, in which the first lateral is connected to the second lateral by means of the first top edge, and a first included angle is formed between the first lateral and a major axis direction of the first rod. Similarly, each of the second raised teeth has a second top edge, a third lateral, and a fourth lateral, in which the third lateral is connected to the fourth lateral by means of the second top edge, and a second included angle is formed between the third lateral and a major axis direction of the second rod. Each range of the first included angle and the second included angle is between 30 and 150 degrees, preferably between 60 and 120 degrees, and more preferably between 85 and 95 degrees. In addition, where the first included angle and the second included angle each range between 85 and 95 degrees, the second lateral of the first raised tooth faces the fourth lateral of the second raised tooth. In addition, the included angle between the first top edge of the first raised tooth and the major axis direction of the first rod is not limited and preferably between 85 and 95 degrees.

In the disclosed spine correction apparatus, the first rod and the second rod are arranged in parallel. In other words, the first rod's major axis is parallel to the second rod's major axis, but the present invention is not limited thereto. A direction in which the extension of the first rod's major axis and the second rod's major axis include an included angle that is between 0 and 45 degrees. The first rod and the second rod are such arranged that the first rod's first zone contacts the second rod's second zone. In addition, the first rod and the second rod are not limited in terms of geometry, and may be round rods, triangular rods, rectangular rods and so on.

In the disclosed spine correction apparatus, the first rod and the second rod each include a plurality of fixing components for fixing the first rod or the second rod to a target spine (i.e. a patient's vertebral body). The fixing components are of no particular limitation. People of ordinary skill in the art may make selection according to materials available or the patient's clinical conditions. For example, the fixing components may be any fixing members commercially available, like rivets, bolts, screws, hook, cable and so on. Therein, screws and nuts are preferable, and examples include monoaxial screws, uniplanar screws and polyaxial screws, etc., and preferably polyaxial screws (e.g. polyaxial pedicle screws) and matching nuts thereof.

In the disclosed spine correction apparatus, a buffer space is provided between the first ring member and the second rod, or between the second ring member and the first rod. The buffer space receives therein a spring element that pushes the first rod's first zone against the second rod's second zone. The spring element may be a compression spring, an extension spring, a torsion spring, a flat spring, a disk spring, and so on, in which a flat spring is preferable. In addition, the way that the first ring member fixed to the first rod and the second ring member fixed to the second rod are not limited, and may be any fixing ways known in the art, such as rivets, bolts, screws, tenon-and-mortise works, and so on. Preferably, bolts and screws are used for this purpose, such as slotted plain bolts, hexagon socket bolts, tapping screw, and set screw, to fix the first ring member and the second ring member to the first rod and the second rod firmly and respectively. Alternatively, the first rod and the first ring member can be integrally formed or integrated as one piece as well as the second rod and the second ring member. This helps to reduce the risk of failure or lower manufacturing costs. In addition, the first ring member and the second ring member may each have more than one through-hole. In other words, the first ring member may further have another first through-hole in addition to the first through-hole, and the second ring member may further have another second through-hole in addition to the second through-hole.

The disclosed spine correction apparatus may further comprise: a third rod having a fourth zone; a third ring member having a third through-hole; and a fourth ring member having a fourth through-hole, wherein, the first rod further has a third zone that is configured to contact the fourth zone, and after the first rod and the third rod pass through the third through-hole of the third ring member and the fourth through-hole of the fourth ring member, the third ring member is fixed to the third rod, and the fourth ring member is fixed to the first rod. In this case, the third zone may have a plurality of third raised teeth, and the fourth zone may have a plurality of fourth raised teeth, wherein the third raised teeth and the fourth raised teeth engage with each other.

Alternatively, in the disclosed spine correction apparatus, the first rod may have a first cross-section in its major axis direction, and the second rod may have a second cross-section in its major axis direction, wherein the first cross-section faces the second cross-section, Therein, the first cross-section and the second cross-section may be equal or different in terms of area, and preferably be equal. In this case, the first rod's first zone is located in the first cross-section, and the second rod's second zone is located in the second cross-section.

The present invention also provides a spine correction kit, which can be optimized to a patient's individual needs and assembled into a correction apparatus (i.e. the foregoing spine correction apparatus). The spine correction kit comprises: a first rod having a first zone; a second rod having a second zone that is configured to contact the first zone; a first ring member having a first through-hole for receiving the first rod and the second rod; and a second ring member having a second through-hole for receiving the first rod and the second rod. The spine correction kit may further comprise: a plurality of fixing components for fixing the first rod and the first ring member together, for fixing the second rod and the second ring member together, for fixing the first rod and a target spine together, or for fixing the second rod and the target spine together; a spring element provided between the first ring member and the second rod, or between the second ring member and the first rod; a third rod having a fourth zone, wherein the first rod further has a third zone that is configured to contact the fourth zone. As the definitions of the components in the spine correction apparatus apply to this kit, repeated description is herein omitted.

With the disclosed spine correction kit, a correction apparatus adapted to a patient's individual scoliosis conditions can be assembled, and then the first rod and the second rod are fixed to the patient's vertebral body where correction is required. Afterward, with the growth of the patient's spine, the correction apparatus extends or contracts in length. Preferably, it extends at the concave side and contracts at the convex side of the patient's spine. The disclosed spine correction apparatus having a simple structure composed of a few parts is easy to be operated and has extensive applications. The kit can be well customized into correction apparatuses depending on patients' individual needs. As compared to the conventional devices, the disclosure is unlikely to fail due to mechanical fatigue, and thus has a longer service life, thereby eliminating the need of repeated surgeries and complications, and having good clinical feasibility.

Other objects, advantages, and novel features of the invention will become more apparent from the following detailed description when taken in conjunction with the accompanying drawings.

BRIEF DESCRIPTION OF THE DRAWINGS

FIG. 2A through 2C show different shapes of the rod according to Embodiment 1 of the present invention.

FIGS. 3A and 3B are top views of raised teeth according to Embodiment 1 of the present invention.

FIG. 4A is a schematic drawing of a ring member according to Embodiment 1 of the present invention.

FIG. 4B through 4D are top views of a variety of ring members according to Embodiment 1 of the present invention.

FIG. 5 is a schematic drawing of raised teeth according to a different aspect of Embodiment 1 of the present invention.

DETAILED DESCRIPTION OF THE PREFERRED EMBODIMENT

For further illustrating the means and functions by which the present invention achieves the certain objectives, the following description, in conjunction with the accompanying drawings and preferred embodiments, is set forth as below to illustrate the implement, structure, features and effects of the subject matter of the present invention.

Embodiment 1 Spine Correction Kit

According to the present invention, a spine correction kit at least comprises: a first rod, a second rod, a first ring member, and a second ring member. Please refer to FIG. 1A through 1E for rods included in the spine correction kit.

Figure 1A:
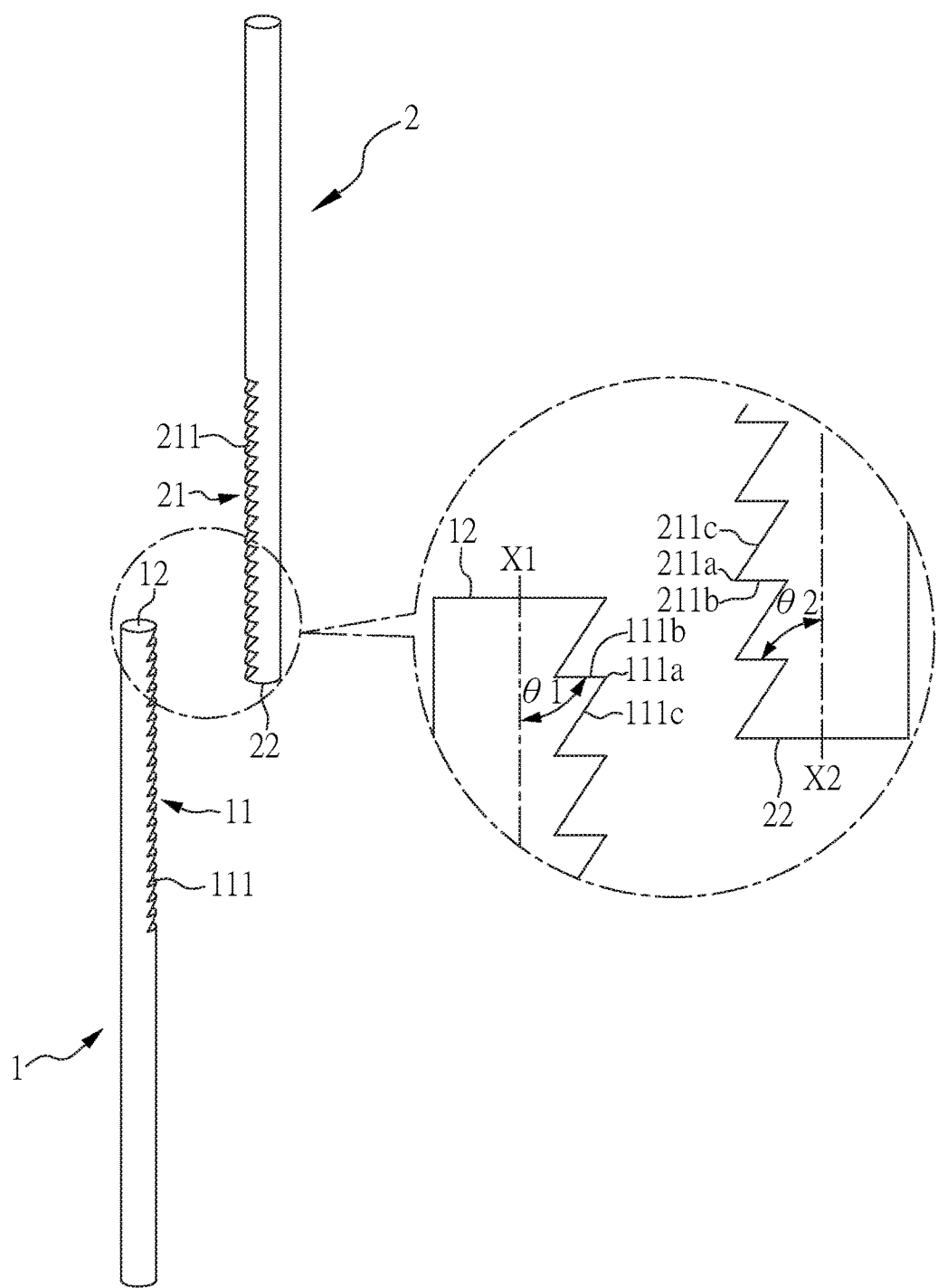
FIG. 1A through 1E are schematic views of plural rods of a spine correction kit according to Embodiment 1 of the present invention.
Figure 1B:
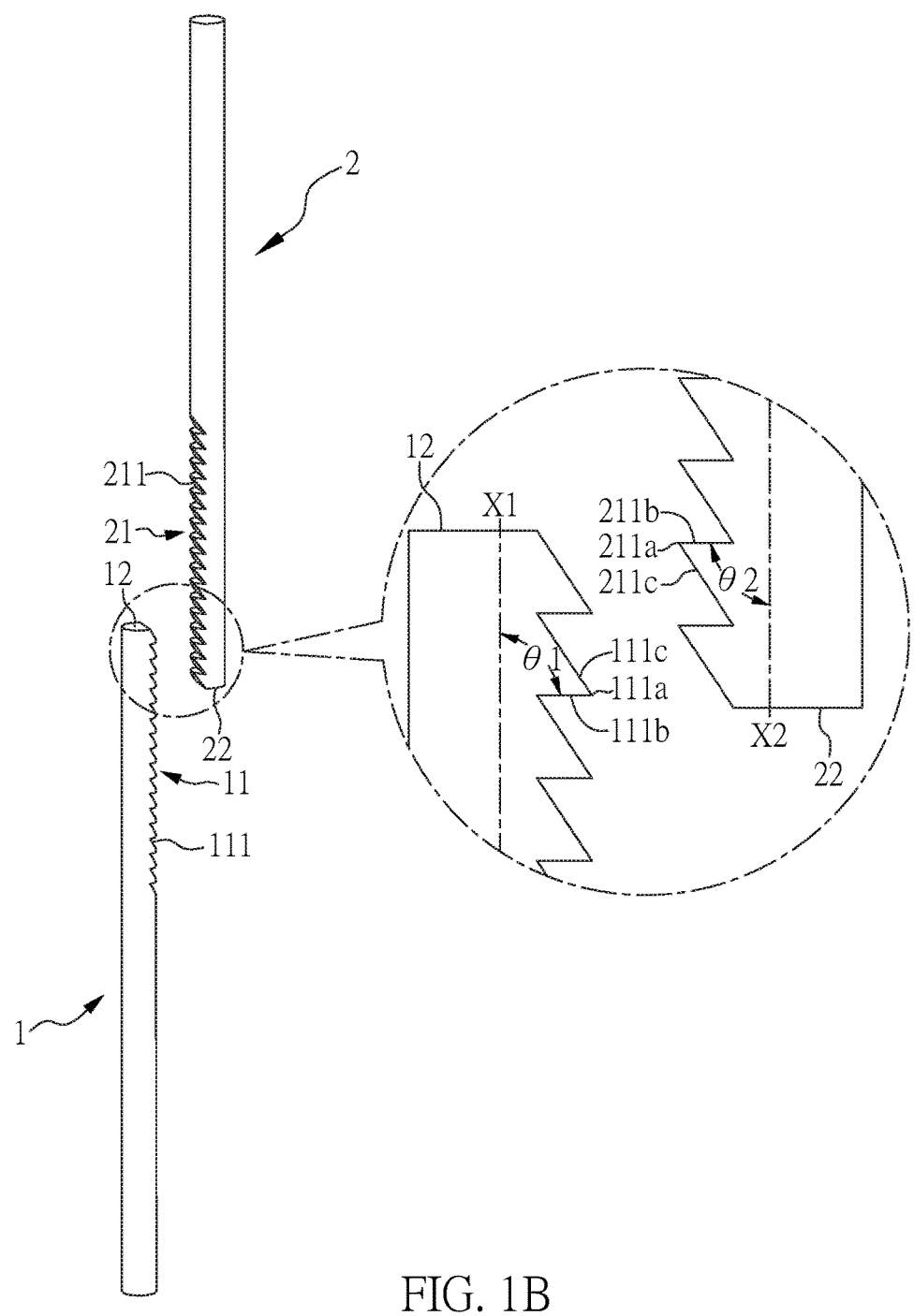
Figure 1C:
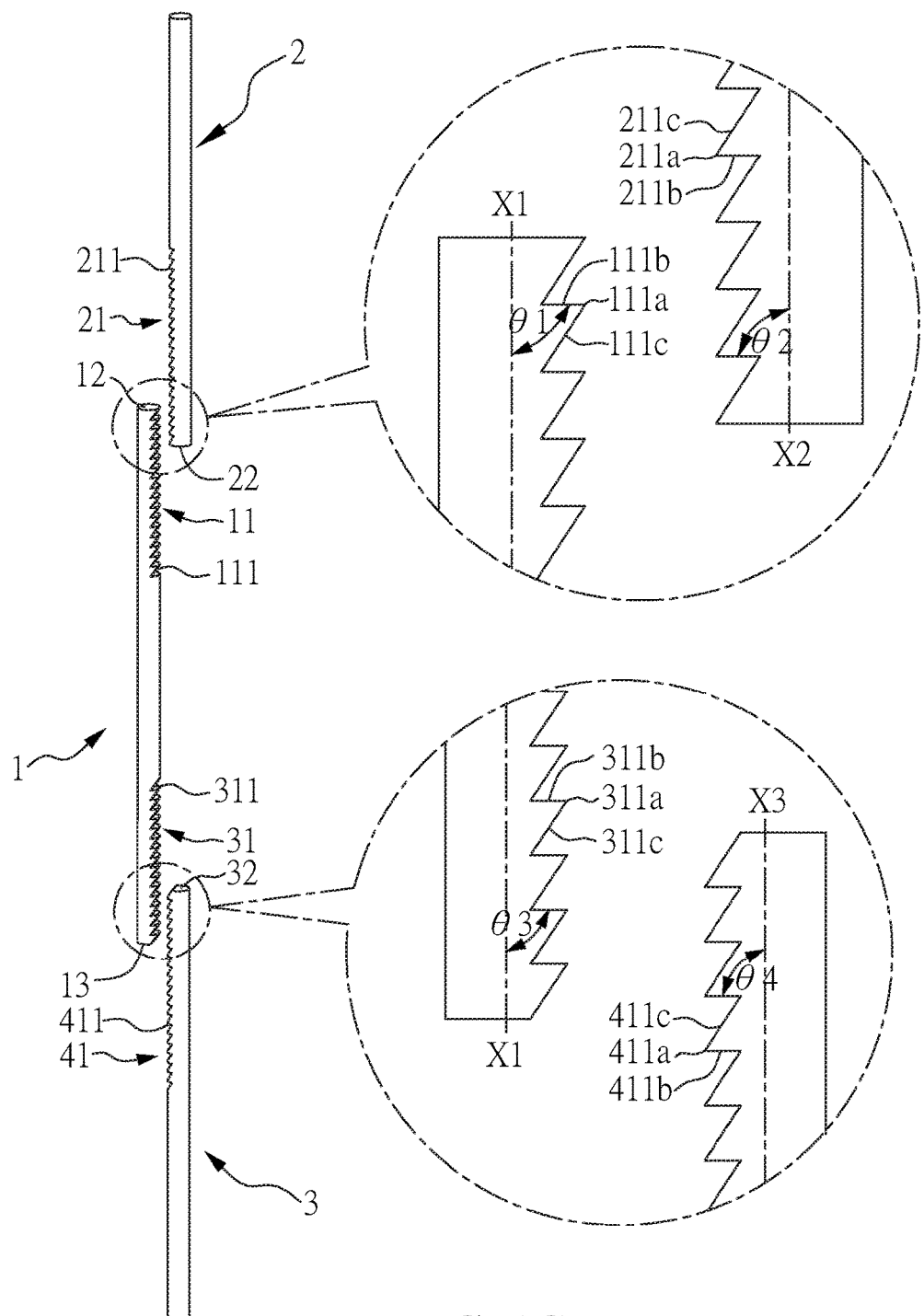

FIGS. 1A, 1B, 1D, and 1E show the first rod and the second rod, while FIG. 1C show the first rod, the second rod, and the third rod. A detailed description thereto is given below.

Referring to FIG. 1A, 1B, the first rod 1 has a first zone 11 in which plural first raised teeth 111 are provided. Each of the first raised teeth 111 has a first top edge 111a, a first lateral 111b, and a second lateral 111c. The first lateral 111b is connected to the second lateral 111c by means of the first top edge 111a. The first lateral 111b and a major axis direction X1 of the first rod 1 include a first included angle θ1. The second rod 2 has a second zone 21 in which plural second raised teeth 211 are provided. Each of the second raised teeth 211 may have a second top edge 211a, a third lateral 211b, and a fourth lateral 211c. The third lateral 211b is connected to the fourth lateral 211c by means of the second top edge 211a. The third lateral 211b and a major axis direction X2 of the second rod 2 include a second included angle θ2. Each range of the first included angle θ1 and the second included angle θ2 is between 85 and 95 degrees. These first raised teeth 111 and these second raised teeth 211 are complementary and configured to engage with each other. Particularly, FIGS. 1A and 1B are different for the following facts. In FIG. 1A, the first lateral 111b of one of the first raised teeth is parallel with the top surface 12 of the first rod 1, and the third lateral 211b of the second raised teeth is parallel with the bottom surface 22 of the second rod 2. In FIG. 1B, one of the first raised teeth 111 has its second lateral 111c formed as an incline and connected to the top surface 12 of the first rod 1, and one of the second raised teeth 211 has its fourth lateral 211c formed as an incline and connected to the bottom surface 22 of the second rod 2.

Alternatively, as shown in FIG. 1C, the first rod 1 further has a third zone 31 in addition to the first zone 11. In the third zone 31, plural third raised teeth 311 are provided. The third raised teeth 311 and the first raised teeth 111 of the first zone 11 are located at the both ends of the first rod 1, respectively. Each of the third raised teeth 311 has a third top edge 311a, a fifth lateral 311b, and a sixth lateral 311c. The fifth lateral 311b is connected to the sixth lateral 311c by means of the third top edge 311a. The fifth lateral 311b and the major axis direction X1 of the first rod 1 include a third included angle θ3. The third raised tooth 311 has its sixth lateral 311c formed as an incline and connected to the bottom surface 13 of the first rod 1. In this case, the spine correction kit further comprises a third rod 3. The third rod 3 has a fourth zone 41 in which plural fourth raised teeth 411 are provided. Each of the fourth raised teeth 411 has a fourth top edge 411a, a seventh lateral 411b, and eighth lateral 411c. The seventh lateral 411b is connected to the eighth lateral 411c by means of the fourth top edge 411a. The seventh lateral 411b and the major axis direction X1 of the first rod 1 include a fourth included angle θ4. Each range of the third included angle θ3 and the fourth included angle θ4 is between 85 and 95 degrees, and the fourth raised tooth 411 has its eighth lateral 411c formed as an incline and connected to the bottom surface 32 of the third rod 3. These third raised teeth 311 and the fourth raised teeth 411 are complementary and configured to engage with each other.

Figure 1D:
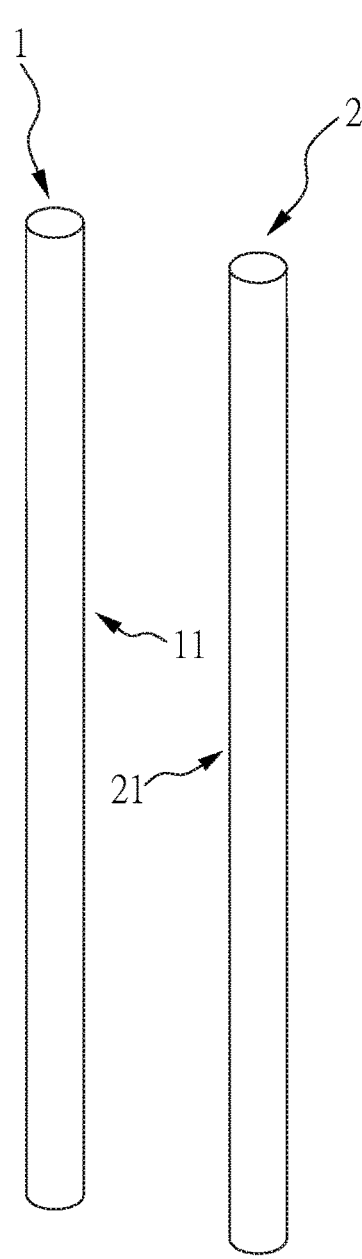
Figure 1E:
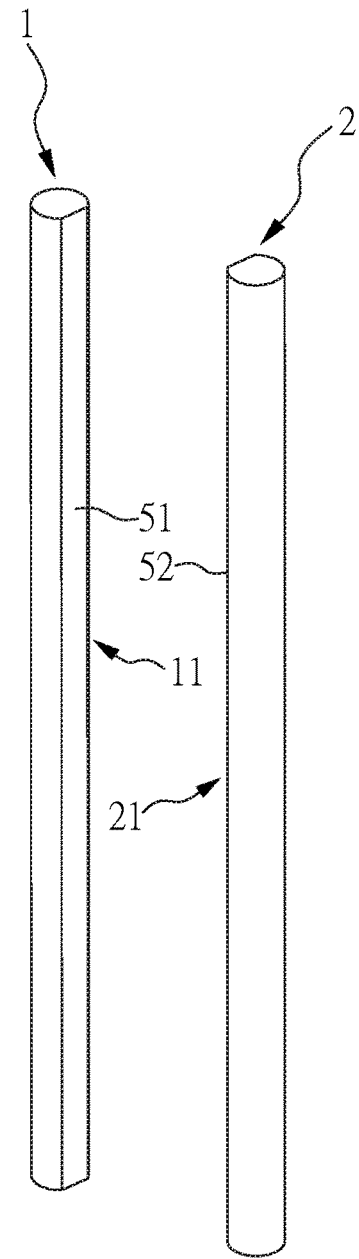

Alternatively, referring to FIG. 1D, the first rod 1 has a first zone 11, and the second rod 2 has a second zone 21. The first zone 11 is configured to contact the second zone 21. Alternatively, as shown in FIG. 1E, the first zone 11 may have a first cross-section 51, and the second zone 21 may have a second cross-section 52. The first cross-section 51 and the second cross-section 52 are equal in terms of area.

In addition, as shown in FIG. 2A through 2C, the first rod, the second rod, and the third rod are not limited in terms of geometry, and each of them may be a round rod (FIG. 2A), a triangular rod (FIG. 2B), or a rectangular rod (FIG. 2C). In the present embodiment, all of these rods are round rods. In addition, FIGS. 3A and 3B are top views of the raised teeth of the rods. In the aspect of FIG. 1A through 1C, the included angle between the first top edge 111a and the major axis direction X1 of the first rod 1, the included angle between the second top edge 211a and the major axis direction X2 of the second rod 2, the included angle between the third top edge 311a and the major axis direction. X1 of the first rod 1, and the included angle between the fourth top edge 411a and the major axis direction X3 of the third rod 3 are not limited. For example, as shown in FIG. 3A, they may be between 85 and 95 degrees, or they may be between 50 and 130 degrees, as shown in FIG. 3B. Preferably, the included angle between the first top edge 111a and the major axis direction X1 of the first rod 1 and the included angle between the second top edge 211a and the major axis direction X2 of the second rod 2 are equal, while the included angle between the third top edge 311a and the major axis direction X1 of the first rod 1 and the included angle between the fourth top edge 411a and the major axis direction X3 of the third rod 3 are equal. In addition, the diameter and volume of each rods, and the shape of each raised teeth are not limited to what recited in the embodiment. People of ordinary skill in the art may further improve the configuration according to practical needs.

Please refer to FIG. 4A as a schematic drawing and FIGS. 4B through 4D as the top views of ring members of the spine correction kit. The spine correction kit may comprise two or more ring members. Each ring member 6 has more than one through-hole 61 for receiving the first rod and the second rod, or the first rod and the third rod. Therefore, the through-hole 61 may be any kinds of forms as long as the first rod and the second rod, or the first rod and the third rod can pass through it. From the top views of FIGS. 4B through 4D, it may be an elliptic through-hole 61 (as shown in FIG. 4B), or two through-holes 61 and 62 (as shown in FIG. 4C), or an 8-like through-hole 61 (as shown in FIG. 4D). Besides, the through-hole 61 has a diameter in its major axis preferably greater than the sum of the diameters of the rods it receives. In other words, when the through-hole 61 receives the first rod and the second rod, the diameter in its major axis is preferably greater than the sum of the diameters of the first rod and the second rod.

In addition, among the first raised teeth and the second raised teeth, the first included angle θ1 between the first lateral 111b and the major axis direction X1 of the first rod 1, and the second included angle θ2 between the third lateral 211b and the major axis direction X2 of the second rod 2 may each range between 30 and 150 degrees, as shown in FIG. 5. The spine correction kit may further comprise a plurality of fixing components for fixing the rods and the ring members, or the rods and the target spine. The types of the fixing components are not particularly limited. In the present embodiment, the rods and the ring member are fixed together using set screws, while the rod and the target spine are fixed together using pedicle screws and corresponding nuts, but not limited thereto. Alternatively, the ring members and the rod may be made as an undetachable member, or may be integrated as one piece according to the feasibility in manufacturing process or clinical needs, thereby minimizing the risk of failure and reducing manufacturing costs.

Embodiment 2 Spine Correction Apparatus

Type 1

Figure 6A:
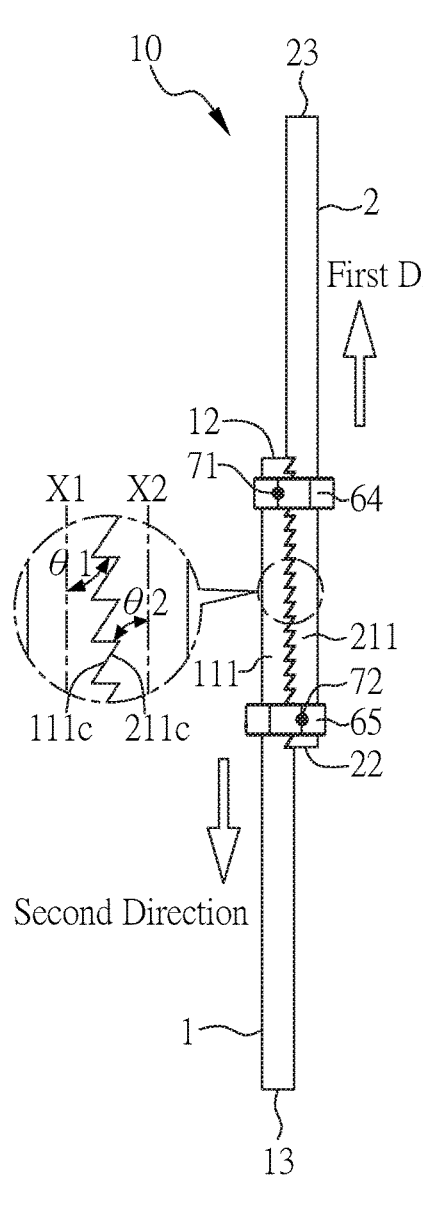
FIG. 6A through 6E are schematic views of a spine correction apparatus according to Embodiment 2 of the present invention.

First, the first rod 1 of FIG. 1A has its top surface 12 facing the first through-hole of the first ring member 64 and the second through-hole of the second ring member 65 (i.e. placed in the first direction as shown in FIG. 6A), and passes through the second through-hole of the second ring member 65 and the first through-hole of the first ring member 64 successively (the configuration of the first ring member 64 and the second ring member 65 are shown in FIG. 4A). A set screw 71 is used to fix the first ring member 64 to the first rod 1, and that is close to the top surface 12. Then, the second rod 2 of FIG. 1A has its bottom surface 22 facing the first through-hole of the first ring member 64 and the second through-hole of the second ring member 65 (i.e. placed in the second direction as shown in FIG. 6A), and passes through the first through-hole of the first ring member 64 and the second through-hole of the second ring member 65 successively. A set screw 72 is used to fix the second ring member 65 to the second rod 2, and that is close to the bottom surface 22. A spine correction apparatus 10 of Type 1 as shown in FIG. 6A is thus assembled. Referring to FIG. 6A, the first raised teeth 111 of the first rod 1 contact the second raised teeth 211 of the second rod 2, and the first raised teeth 111 and the second raised teeth 211 engage with each other. The second lateral 111c of the first raised tooth 111 faces the fourth lateral 211c of the second raised tooth 211. In this case, by applying a pulling force in the second direction to the first rod 1 at the bottom surface 13, or applying a pulling force in the first direction to the second rod 2 at the top surface 23, the first rod 1 is moved in the second direction, or the second rod 2 is moved in the first direction, so the spine correction apparatus 10 is extended. However, a pushing force in the first direction applied to the first rod 1 at the bottom surface 13, or a pushing force in the second direction applied to the second rod 2 at the top surface 23, the first rod 1 is hard to move in the second direction, and the second rod 2 is hard to move in the first direction since each range of the first included angle θ1 and the second included angle θ2 is between 85 and 95 degrees. So the spine correction apparatus 10 is hard to be contracted.

Type 2

Figure 6B:
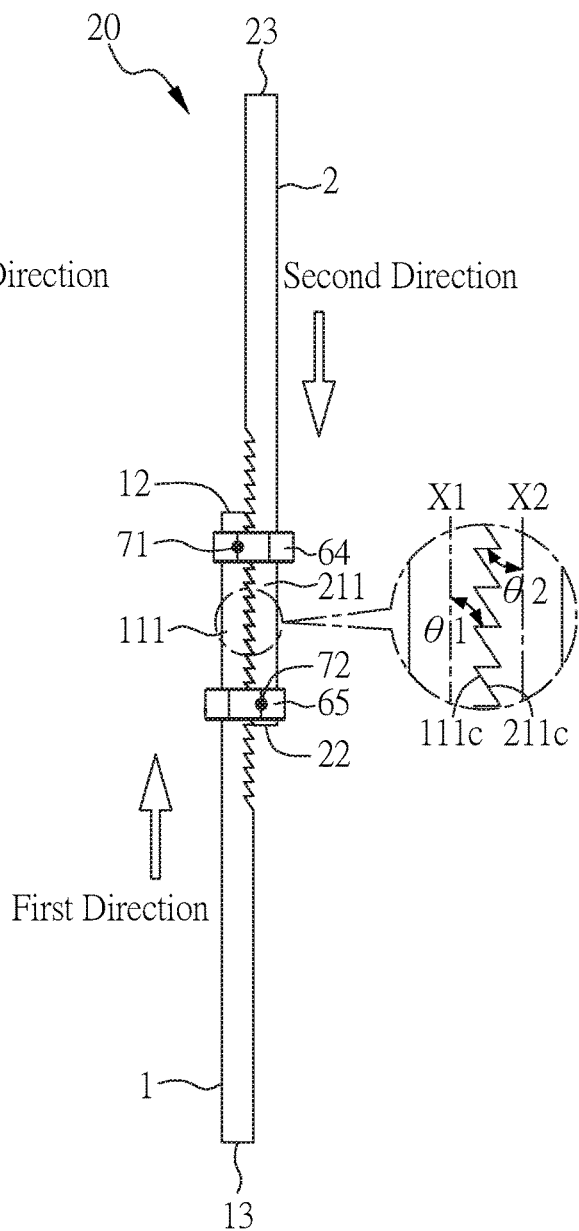

First, the first rod 1 of FIG. 1B has its top surface 12 facing the first through-hole of the first ring member 64 and the second through-hole of the second ring member 65 (i.e. placed in the first direction as shown in FIG. 6B), and passes through the first through-hole of the first ring member 64 and the second through-hole of the second ring member 65 successively (the configuration of the first ring member 64 and the second ring member 65 are shown in FIG. 4A). A set screw 71 is used to fix the first ring member 64 to the first rod 1. Then, the second rod 2 of FIG. 1B has its bottom surface 22 facing the first through-hole of the first ring member 64 and the second through-hole of the second ring member 65 (i.e. placed in the second direction as shown in FIG. 6B), and passes through the second through-hole of the second ring member 65 and the first through-hole of the first ring member 64 successively. A set screw 72 is used to fix the second ring member 65 to the second rod 2. A spine correction apparatus 20 of Type 2 as shown in FIG. 6B is thus assembled. Referring to FIG. 6B, the first raised teeth 111 of the first rod 1 contact the second raised teeth 211 of the second rod 2, and the first raised tooth 111 and the second raised tooth 211 engage with each other. The second lateral 111c of the first raised tooth 111 faces the fourth lateral 211c of the second raised tooth 211. In this case, by applying a pulling force in the first direction to the first rod 1 at the bottom surface 13, or applying a pulling force in the second direction to the second rod 2 at the top surface 23, the first rod 1 is moved in the first direction, or the second rod 2 is moved in the second direction, so the spine correction apparatus 20 is contracted. However, a pulling force in the second direction applied to the first rod 1 at the bottom surface 13, or a pulling force in the first direction applied to the second rod 2 at the top surface 23, the first rod 1 is hard to move in the second direction, and the second rod 2 is hard to move in the first direction since each range of the first included angle θ1 and the second included angle θ2 is between 85 and 95 degrees. So the spine correction apparatus 20 is hard to be extended.

Type 3

Figure 6C:
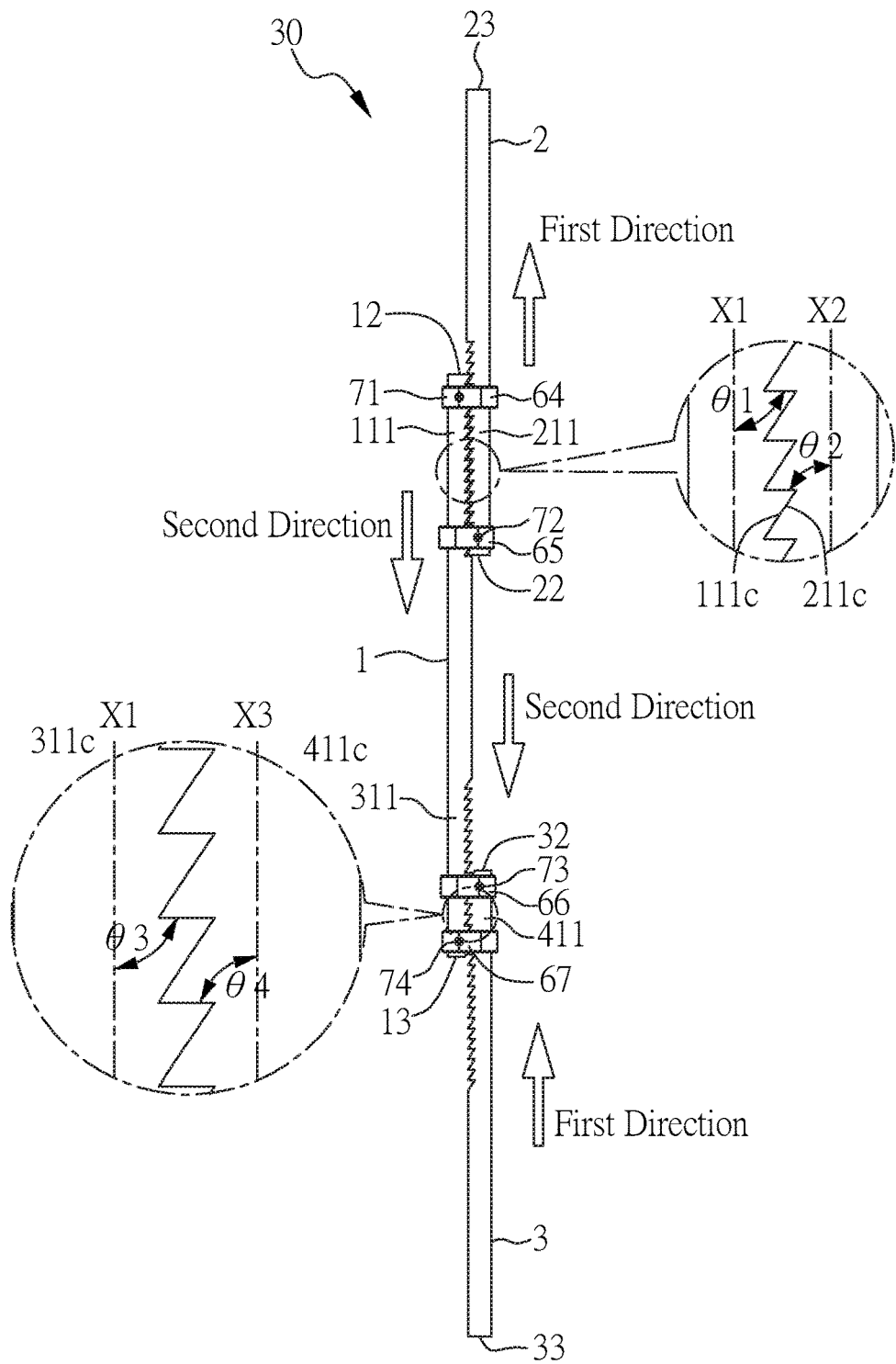

First, the first rod 1 of FIG. 1C has its top surface 12 facing the first through-hole of the first ring member 64 and the second through-hole of the second ring member 65 (i.e. in the first direction as shown in FIG. 6C), and passes through the second through-hole of the second ring member 65 and the first through-hole of the first ring member 64 successively (the configuration of the first ring member 64 and the second ring member 65 are shown in FIG. 4A). A set screw 71 is used to fix the first ring member 64 to the first rod L Then, the first rod 1 has its bottom surface 13 facing the third through-hole of the third ring member 66 and the fourth through-hole of the fourth ring member 67 (i.e. in the second direction as shown in FIG. 6C), and passes through the third through-hole of the third ring member 66 and the fourth through-hole of the fourth ring member 67 successively (the third ring member 66 and the fourth ring member 67 are both structurally like those shown in FIG. 4A). A set screw 74 is used to fix the fourth ring member 67 to the first rod 1. Then, the second rod 2 of FIG. 1C has its bottom surface 22 facing the first through-hole of the first ring member 64 and the second through-hole of the second ring member 65 (i.e. in the second direction as shown in FIG. 6C), and passes through first through-hole of the first ring member 64 and the second through-hole of the second ring member 65 successively. A set screw 72 is used to fix the second ring member 65 to the second rod 2. At last, the third rod 3 of FIG. 1C has its top surface 32 facing the third through-hole of the third ring member 66 and the fourth through-hole of the fourth ring member 67 (i.e. in the first direction as shown in FIG. 6C), and passes through the fourth through-hole of the fourth ring member 67 and the third through-hole of the third ring member 66 successively. A set screw 73 is used to fix the third ring member 66 to the third rod 3. A spine correction apparatus 30 of Type 3 as shown in FIG. 6C is thus assembled.

Referring to FIG. 6C, the first raised teeth 111 of the first rod 1 contact the second raised teeth 211 of the second rod 2, and the first raised teeth 111 and the second raised teeth 211 engage with each other. The second lateral 111c of the first raised tooth 111 faces the fourth lateral 211c of the second raised tooth 211. At the same time, the third raised teeth 311 of the first rod 1 contact the fourth raised teeth 411 of the third rod 3, and the first raised teeth 311 and the fourth raised teeth 411 engage with each other. The sixth lateral 311c of the first raised tooth 111 faces the eighth lateral 411c of the third raised tooth 411. In this case, by applying a pulling force in the second direction to the first rod 1 at the bottom surface 13, or applying a pulling force in the first direction to the second rod 2 at the top surface 23, the first rod 1 is moved in the second direction, or the second rod 2 is moved in the first direction, so the spine correction apparatus 30 is extended. In addition, by applying a pushing force in the second direction to the first rod 1 at the top surface 12, or applying a pushing force in the first direction to the third rod 3 at the bottom surface 33, the first rod 1 is moved in the second direction, or the third rod 3 is moved in the first direction, so the spine correction apparatus 30 is contracted. Thereby, the spine correction apparatus 30 of Type 3 is a dual-functional design, the spine correction apparatus 30 can be extended at the end where the first rod 1 and the second rod 2 contact, and can be contracted at the other end where the first rod 1 and the third rod 3 contact.

On the other hand, a pushing force in the first direction applied to the first rod 1 at the bottom surface 13, or a pushing force in the second direction applied to the second rod 2 at the top surface 23, the first rod 1 is hard to move in the first direction, and the second rod 2 is hard to move in the second direction since each range of the first included angle θ1 and the second included angle θ2 is between 85 and 95 degrees. Where a pulling force in the first direction is applied to the first rod 1 at the top surface 12, or a pulling force in the second direction is applied to the third rod 3 at the bottom surface 33, the first rod 1 is hard to move in the first direction, and the third rod 3 is hard to move in the second direction since each range of the first included angle θ1 and the second included angle θ2 is between 85 and 95 degrees. Thus, it is hard to contract the spine correction apparatus 30 at the end where the first rod 1 and the second rod 2 contact, and it is hard to extend the spine correction apparatus 30 at the other end where the first rod 1 and the third rod 3 contact.

Type 4

Figure 6D:
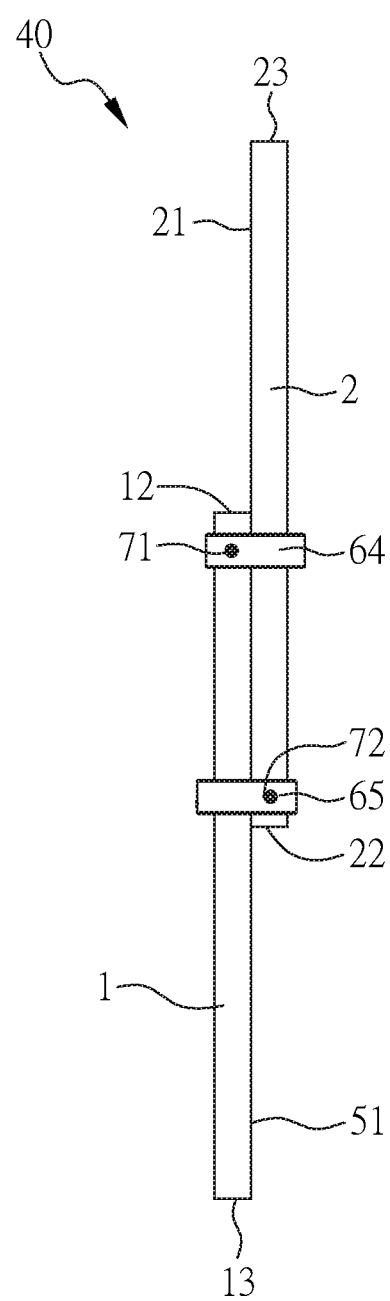

First, the first rod 1 of FIG. 1D has its top surface 12 facing the first through-hole of the first ring member 64 and the second through-hole of the second ring member 65 (i.e. in the first direction as shown in FIG. 6D), and passes through the second through-hole of the second ring member 65 and the first through-hole of the first ring member 64 successively (the configuration of the first ring member 64 and the second ring member 65 are shown in FIG. 4A). A set screw 71 is used to fix the first ring member 64 to the first rod 1. Then, the second rod 2 of FIG. 1D has its bottom surface 22 facing the first through-hole of the first ring member 64 and the second through-hole of the second ring member 65 (i.e. in the second direction as shown in FIG. 6D), and passes through first through-hole of the first ring member 64 and the second through-hole of the second ring member 65 successively. A set screw 72 is used to fix the second ring member 65 to the second rod 2. A spine correction apparatus 40 of Type 4 as shown in FIG. 6D is thus assembled. Referring to FIG. 6D, the first zone 11 of the first rod 1 contacts the second zone 21 of the second rod 2. In this case, by applying a pulling force in the second direction to the first rod 1 at the bottom surface 13, or applying a pulling force in the first direction to the second rod 2 at the top surface 23, the first rod 1 is moved in the second direction, or the second rod 2 is moved in the first direction, so the spine correction apparatus 40 is extended. Alternatively, by applying a pushing force in the first direction to the first rod 1 at the bottom surface 13, or applying a pushing force in the second direction to the second rod 2 at the top surface 23, the first rod 1 is moved in the first direction, or the second rod 2 is moved in the second direction, so the spine correction apparatus 40 is contracted. Thus, the spine correction apparatus 40 of Type 4 is a dual-directional design and can be extended or contracted according to the direction of the applying force.

Type 5

Figure 6E:
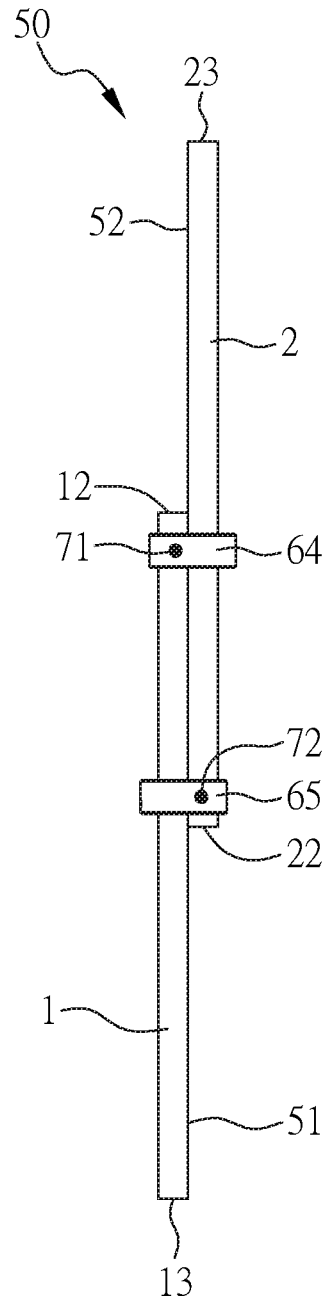

First, the first rod 1 of FIG. 1E has its top surface 12 facing the first through-hole of the first ring member 64 and the second through-hole of the second ring member 65 (i.e. the first direction as shown in FIG. 6E), and passes through the second through-hole of the second ring member 65 and the first through-hole of the first ring member 64 successively (the configuration of the first ring member 64 and the second ring member 65 are shown in FIG. 4A). A set screw 71 is used to fix the first ring member 64 to the first rod 1. Then, the second rod 2 of FIG. 1D has its bottom surface 22 facing the first through-hole of the first ring member 64 and the second through-hole of the second ring member 65 (i.e. in the second direction as shown in FIG. 6E), and passes through first through-hole of the first ring member 64 and the second through-hole of the second ring member 65 successively. A set screw 72 is used to fix the second ring member 65 to the second rod 2. A spine correction apparatus 50 of Type 5 as shown in FIG. 6E is thus assembled. Referring to FIG. 6E, the first cross-section 51 of the first rod 1 contacts the second cross-section 52 of the second rod 2. In this case, by applying a pulling force in the second direction to the first rod 1 at the bottom surface 13, or applying a pulling force in the first direction to the second rod 2 at the top surface 23, the first rod 1 is moved in the second direction, or the second rod 2 is moved in the first direction, so the spine correction apparatus 50 is extended. Alternatively, by applying a pushing force in the first direction to the first rod 1 at the bottom surface 13, or applying a pushing force in the second direction to the second rod 2 at the top surface 23, the first rod 1 is moved in the first direction, or the second rod 2 is moved in the second direction, so the spine correction apparatus 50 is contracted. Thus, the spine correction apparatus 50 of Type 5 is a dual-direction design, and capable of extending or contracting according to the direction of the applying force.

In Embodiment 2, the first rod, the second rod, and the third rod are substantively parallel to each other. In other words, the major axes of the first rod, the second rod, and the third rod are parallel to each other. However, the present invention is not limited thereto, as long as the first zone of the first rod contacts the second zone of the second rod, and the third zone of the first rod contacts the fourth zone of the third rod.

[Clinical Case 1]

Figure 7A:
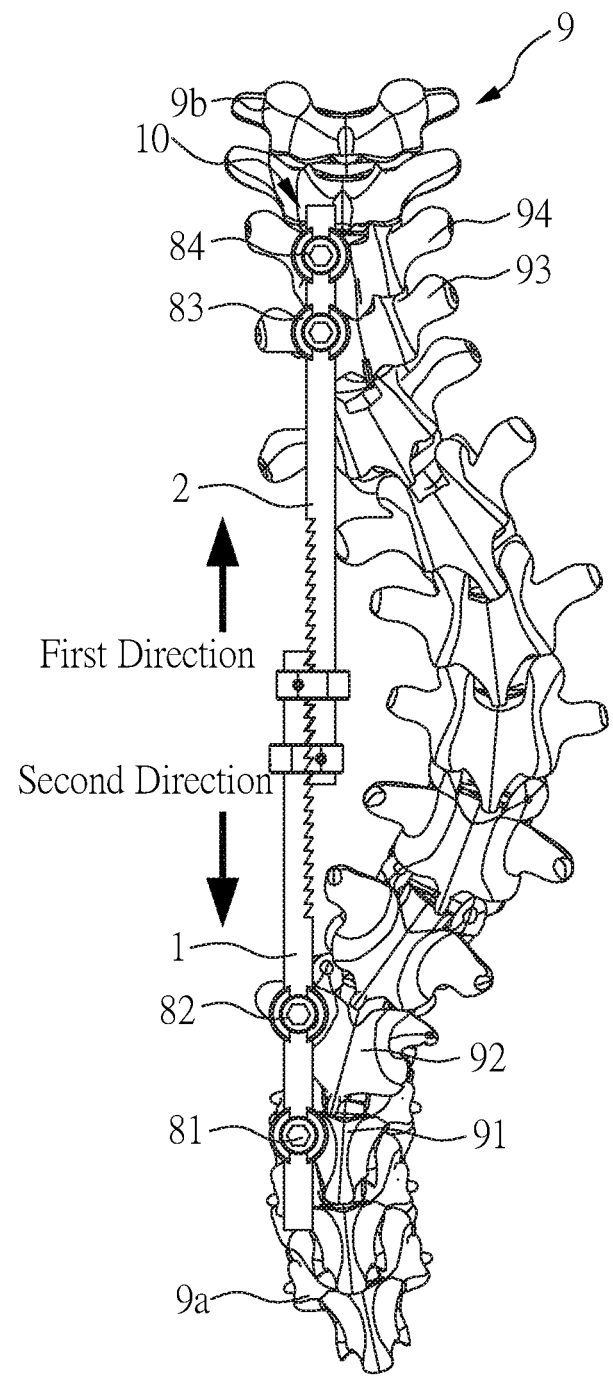
FIG. 7A is a schematic drawing showing correction of C-type scoliosis according to Clinical Case 1 of the present invention.

For a patient with C-shaped scoliosis, correction surgery involves installing the spine correction apparatus 10 of Type 1 as shown in FIG. 6A at the concave side of the spine. Referring to FIG. 7A, the patient's spine with C-shaped scoliosis is referred to as the target spine 9, and has a first end 9a and second end 9b. The spine correction apparatus 10 of Type 1 shown in FIG. 6A is used to one's spine correction. Particularly, the first rod 1 is fixed to the first vertebral body 91 using the fixing component 81 at the concave side of the target spine 9, and is fixed to the second vertebral body 92 using the fixing component 82 at the concave side of the target spine 9. The second rod 2 is fixed to the third vertebral body 93 using the fixing component 83 at the concave side of the target spine 9, and is fixed to the fourth vertebral body 94 using the fixing component 84 at the concave side of the target spine 9. Therein, the first vertebral body 91 and the second vertebral body 92 are close to the first end 9a of the target spine 9, while the third vertebral body 93 and the fourth vertebral body 94 are close to the second end 9b of the target spine 9.

Figure 7B:
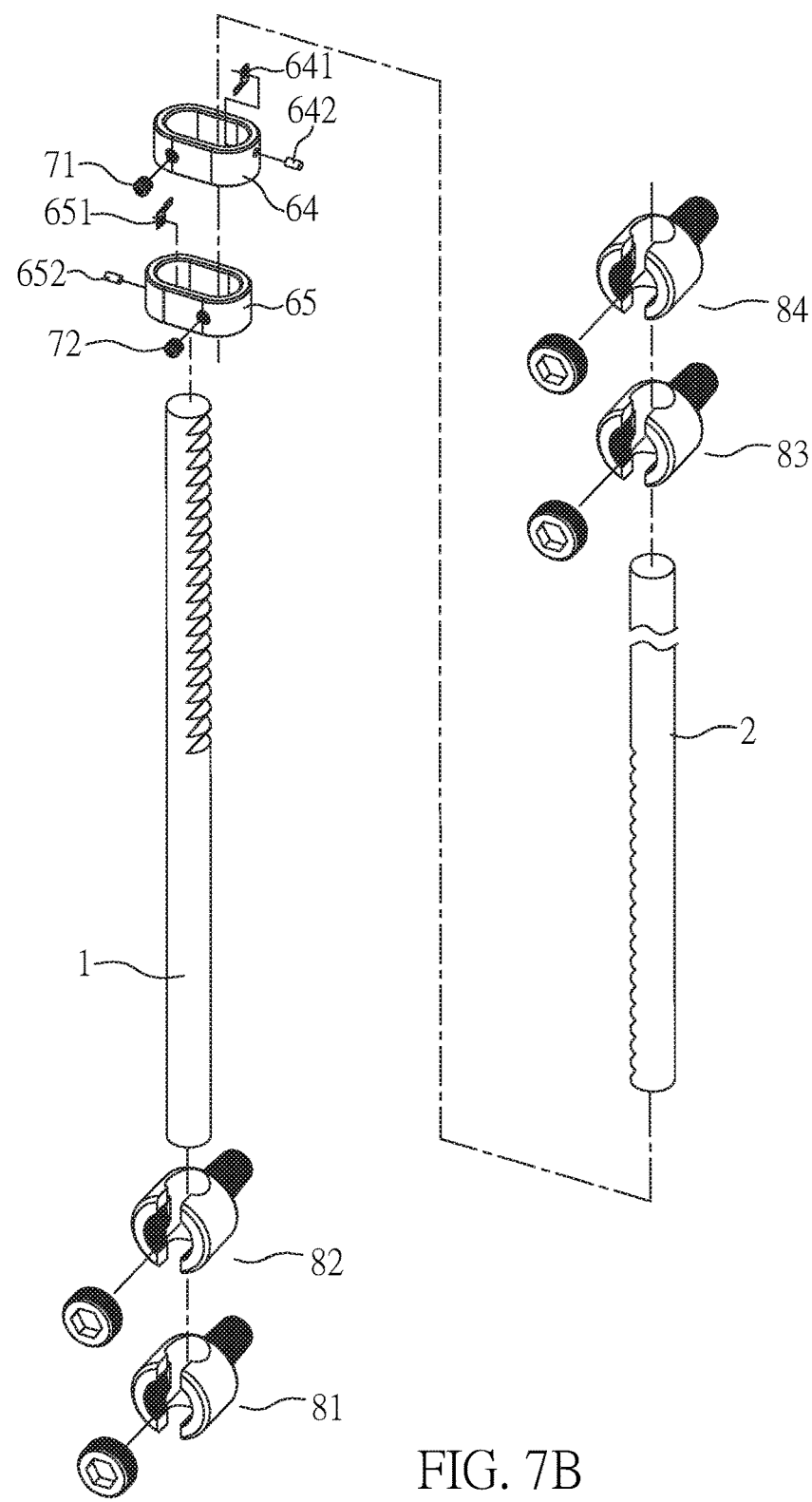
FIGS. 7B and 7C are an exploded view and a front view of the spine correction apparatus used in Clinical Case 1 of the present invention, respectively.
Figure 7C:
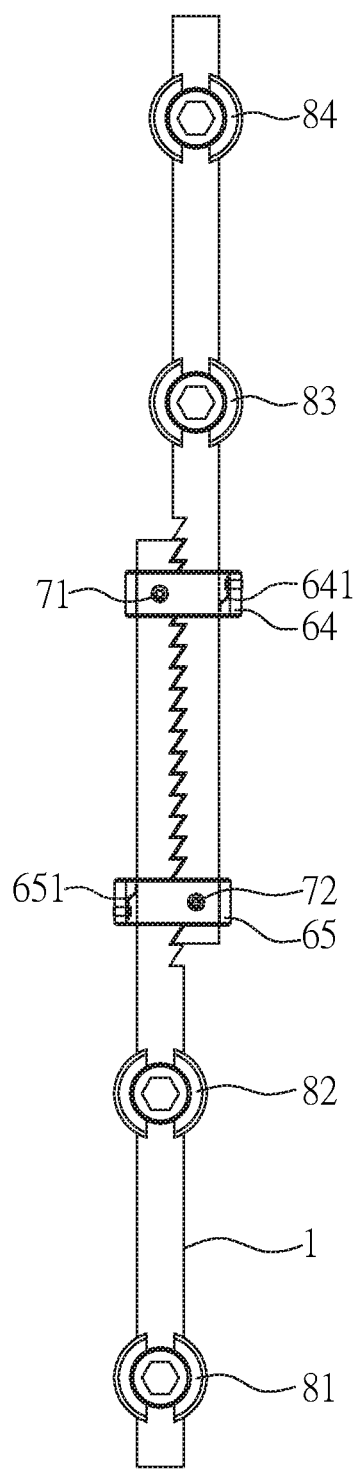

FIG. 7B and FIG. 7C are exploded and the front views of the spine correction apparatus 10 of Type 1. Therein, a buffer space may be provided between the second ring member 65 and the first rod 1, and another buffer space may be provided between the first ring member 64 and the second rod 2. The buffer spaces may accommodate therein flat springs 641, 651, respectively, which are fixed to the first ring member 64 and the second ring member 65 by means of pins 642, 652, respectively, so as to keep the two rods further close. In addition, the fixing components 81, 82, 83 and 84 used in the present embodiment are pedicle screws and their matching nuts as described in the spine correction kit of Embodiment 1, as shown in FIGS. 7B and 7C. It is to be noted, each of the rods not necessarily to use two fixing components to fixed to the vertebral body. Instead, one or more than one fixing components shall be used according to the patient's clinical conditions.

With the foregoing arrangement, as the target spine 9 grows, the first rod 1 fixed to the first end 9a of the target spine 9 receives a pulling force in the second direction, and the second rod 2 fixed to the second end 9b of the target spine 9 receives a pulling force in the first direction. In this way, the spine correction apparatus 10 extends with the growth of the target spine 9, thereby effectively correcting scoliosis and providing sufficient support to the spine.

Figure 7D:
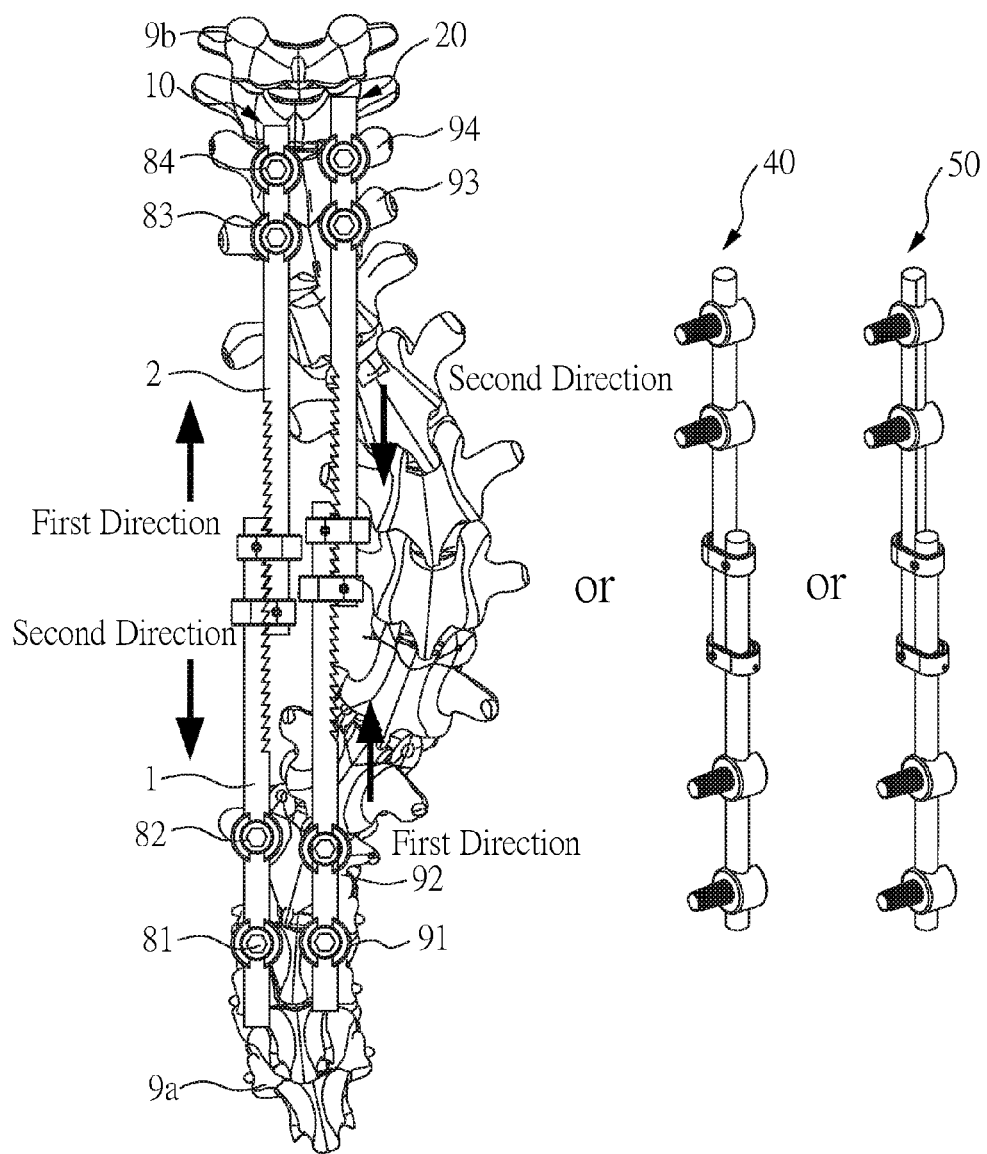
FIG. 7D is a schematic drawing showing correction of C-type scoliosis according to another aspect of Clinical Case 1 of the present invention.

Alternatively, another spine correction apparatus may be installed at the convex side of the target spine 9. As shown in FIG. 7D, the spine correction apparatus 20 of Type 2, the spine correction apparatus 40 of Type 4 or the spine correction apparatus 50 of Type 5 may be installed at the convex side of the target spine 9. Similarly, as learned from the description related to FIG. 7A, when the spine correction apparatus 20 of Type 2, the spine correction apparatus 40 of Type 4 or the spine correction apparatus 50 of Type 5 is installed at the convex side of the target spine 9, fixing components are used to fix the first rod and the second rod to the vertebral bodies at the first end 9a and the second end 9b of the target spine 9, respectively. In this way, at the concave side of the target spine 9, the spine correction apparatus 10 extends with the growth of the target spine 9, and at the convex side of the target spine 9, the spine correction apparatus 20 of Type 2, the spine correction apparatus 40 of Type 4 or the spine correction apparatus 50 of Type 5 contracts with the growth of the target spine 9. By installing proper correction apparatuses at the concave side and the convex side of the target spine 9, the efficiency of the correction surgery can be significantly improved.

[Clinical Case 2]

Figure 8A:
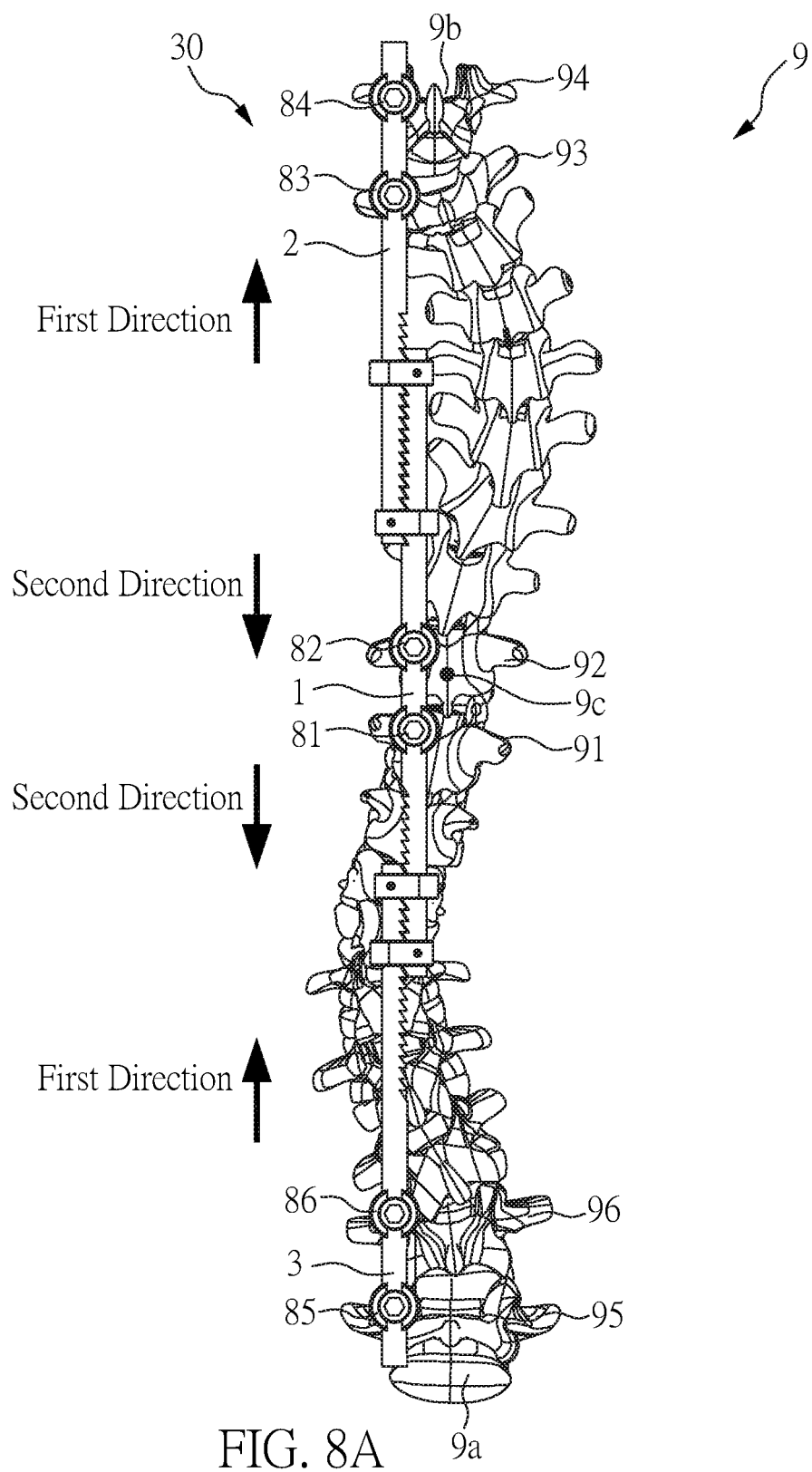
FIG. 8A is a schematic drawing showing correction of S-type scoliosis according to Clinical Case 2 of the present invention.

For a patient with S-shaped scoliosis, correction surgery involves installing the spine correction apparatus 30 of Type 3 as shown in FIG. 6C. Referring to FIG. 8A, the patient's spine with S-shaped scoliosis is referred to as the target spine 9, and has a first end 9a, a second end 9b and a center point 9c (the center point 9c is the center point of the link between the first end 9a and the second end 9b, or the turning point of the S-shaped scoliosis). The spine correction apparatus 30 of Type 3 shown in FIG. 6C is used. The first rod 1 is fixed to the first vertebral body 91 of the target spine 9 using the fixing component 81 at the border between the concave and convex sides of the target spine 9, and is fixed to the second vertebral body 92 of the target spine 9 using the fixing component 82 at the border between the concave and convex sides of the target spine 9. The second rod 2 is fixed to the third vertebral body 93 using the fixing component 83 at the concave side of the target spine 9, and is fixed to the fourth vertebral body 94 using the fixing component 84 at the concave side of the target spine 9. The third rod 3 is fixed to the fifth vertebral body 95 using the fixing component 85 at the convex side of the target spine 9, and is fixed to the sixth vertebral body 96 using the fixing component 86 at the convex side of the target spine 9. Therein, the first vertebral body 91 and the second vertebral body 92 are close to the center point 9c of the target spine 9, while the third vertebral body 93 and the fourth vertebral body 94 are close to the second end 9b of the target spine 9, while the fifth vertebral body 95 and the sixth vertebral body 96 are close to the first end 9a of the target spine 9. In addition, the fixing components 81, 82, 83, 84, 85 and 86 used in the present embodiment are pedicle screws and their matching nuts as described in the spine correction kit of Embodiment 1.

With the foregoing arrangement, as the target spine 9 grows, the first rod 1 fixed to the center point 9c of the target spine 9 receives a pulling force in the second direction, and the second rod 2 fixed to the second end 9b of the target spine 9 receives a pulling force in the second rod 2. In this way, the spine correction apparatus 30 extends at the end where the first rod 1 and the second rod 2 contact as the target spine 9 grows. In addition, when the target spine 9 grows, the first rod 1 fixed to the center point 9c of the target spine 9 receives a pushing force in the second direction, and the third rod 3 fixed to the first end 9a of the target spine 9 receives a pushing force in the first direction. In this way, contraction happens from the end where the first rod 1 and the third rod 3 contacts with the growth of the target spine 9, thereby effectively correcting scoliosis and providing sufficient support to the spine.

Figure 8B:
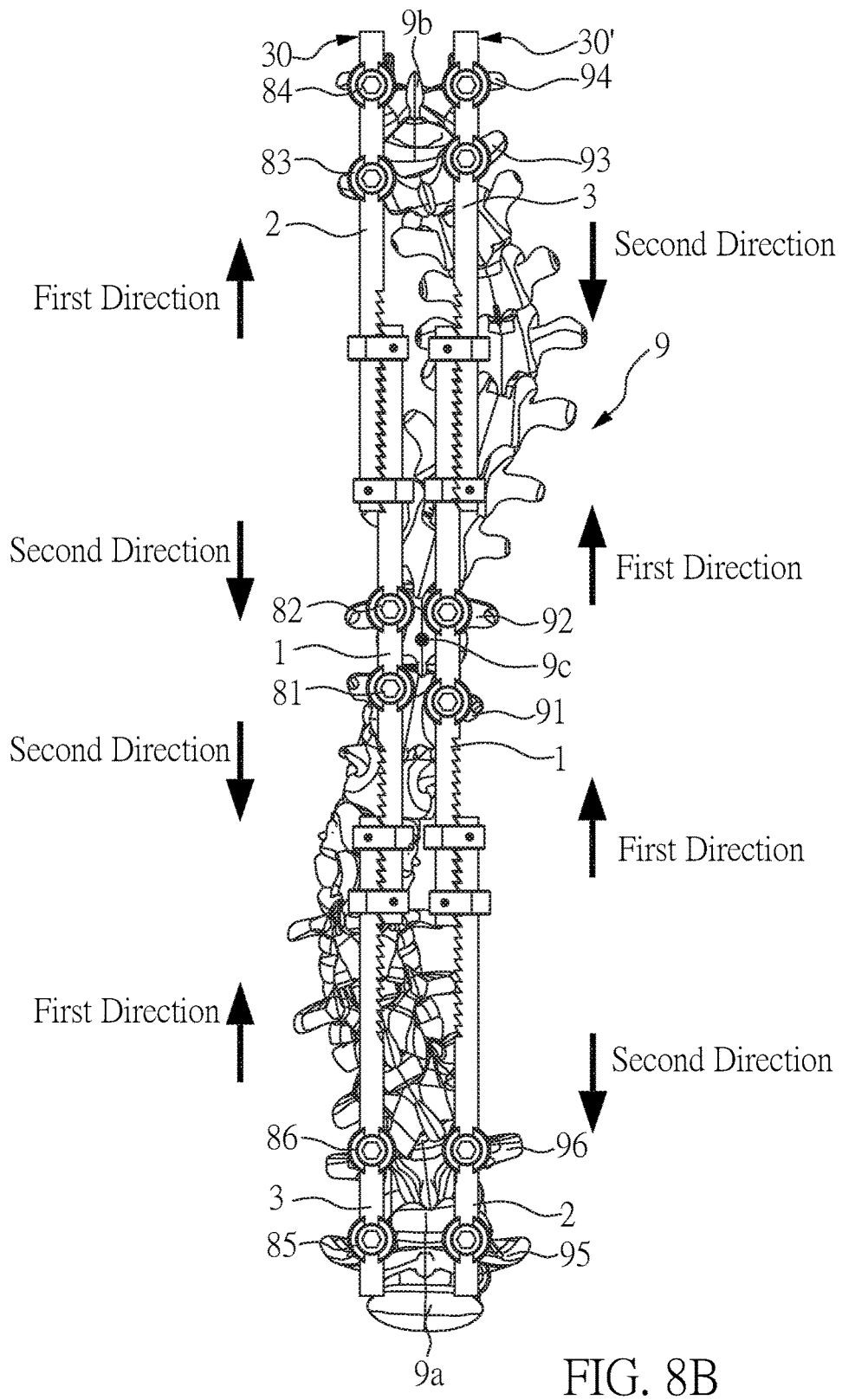
FIG. 8B is a schematic drawing showing correction of S-type scoliosis according to another aspect of Clinical Case 2 of the present invention.

Alternatively, another spine correction apparatus may be installed at the other side of the target spine 9. As shown in FIG. 8B, one spine correction apparatus 30 of Type 3 is installed at one side of the target spine 9, while another spine correction apparatus 30' of Type 3, as the spine correction apparatus 30 shown in FIG. 7A, is reversely installed at the other side of the target spine 9. As described above, fixing components are used to fix the first, second, and third rods of the spine correction apparatus 30' to the vertebral body at the center point 9c, the first end 9a, and the second end 9b of the target spine 9, respectively. In this manner, the efficiency of the correction surgery can be significantly improved.

The disclosed spine correction apparatus including two rods with mutually complementary raised teeth ensure the spine with sufficient support by the engagement with the raised teeth. Also, with the specific range of the angles between the raised teeth and the major axes, the two rods are limited to move oppositely as the spine grows and thereby make the overall length increase or decrease. In addition, when the spine correction apparatus is implanted into a patient's body, with the assistance from the contracture of soft tissue or from the flat spring, the two rods are bound tightly and unlikely to come off from each other.

The present invention has been described with reference to the preferred embodiments, and it is understood that the embodiments are not intended to limit the scope of the present invention. Moreover, the contents disclosed herein should be readily understood and can be implemented by a person skilled in the art, all equivalent changes or modifications which do not depart from the concept of the present invention should be encompassed by the appended claims.

What is claimed is:

1. A spine correction apparatus, comprising:
a first rod having a first zone;
a second rod having a second zone that is configured to contact the first zone;
a first ring member having a first through-hole; and
a second ring member having a second through-hole, wherein, the first rod and the second rod pass through the first through-hole of the first ring member and through the second through-hole of the second ring member, in which the first ring member is fixed to the first rod, and the second ring member is fixed to the second rod; the first zone has a plurality of first raised teeth, and the second zone has a plurality of second raised teeth, in which the first raised teeth and the second raised teeth are configured to engage with each other; each of the first raised teeth is consist of a first top edge, a first lateral, and a second lateral, in which the first lateral is connected to the second lateral by means of the first top edge, and a first included angle formed between the first lateral and a major axis direction of the first rod ranges between 85 and 95 degrees; each of the second raised teeth is consist of a second top edge, a third lateral, and a fourth lateral, in which the third lateral is connected to the fourth lateral by means of the second top edge, and a second included angle formed between the third lateral and a major axis direction of the second rod ranges between 85 and 95 degrees; and the second lateral and the fourth lateral are inclines configured to allow relative movement between the first rod and the second rod after the first raised teeth and the second raised teeth engage with each other.

2. The spine correction apparatus of claim 1, wherein the second lateral is configured to face the fourth lateral.

3. The spine correction apparatus of claim 1, wherein the first rod and the second rod are such installed that they are parallel to each other.

4. The spine correction apparatus of claim 1, wherein the first rod and the second rod each have a plurality of fixing components.

5. The spine correction apparatus of claim 1, wherein a spring element is provided between the first ring member and the second rod, or between the second ring member and the first rod.

6. The spine correction apparatus of claim 1, further comprising:
a third rod having a fourth zone;
a third ring member having a third through-hole; and
a fourth ring member having a fourth through-hole,
wherein, the first rod further has a third zone that is configured to contact the fourth zone, and after the first rod and the third rod pass through the third through-hole of the third ring member and the fourth through-hole of the fourth ring member, the third ring member is fixed to the third rod, and the fourth ring member is fixed to the first rod.

7. The spine correction apparatus of claim 6, wherein the third zone has a plurality of third raised teeth, and the fourth zone has a plurality of fourth raised teeth, in which the third raised teeth and the fourth raised teeth are configured to engage with each other.

8. The spine correction apparatus of claim 1, wherein the first rod has a first cross-section in its major axis direction, and the second rod has a second cross-section in its major axis direction, in which the first cross-section is configured to face the second cross-section.

9. The spine correction apparatus of claim 8, wherein the first cross-section and the second cross-section are equal in terms of area.

10. The spine correction apparatus of claim 1, wherein an acute angle formed between the second lateral and the major axis direction of the first rod, and an acute angle formed between the fourth lateral and the major axis direction of the second rod.

11. A spine correction kit, comprising:
a first rod having a first zone;
a second rod having a second zone that is configured to contact the first zone;
a first ring member having a first through-hole for receiving the first rod and the second rod; and
a second ring member having a second through-hole for receiving the first rod and the second rod;
wherein the first zone has a plurality of first raised teeth, and the second zone has a plurality of second raised teeth, in which the first raised teeth and the second raised teeth are complementary with each other; each of the first raised teeth consists of a first top edge, a first lateral, and a second lateral, in which the first lateral is connected to the second lateral by means of the first top edge, a first included angle formed between the first lateral and a major axis direction of the first rod ranges between 85 and 95 degrees; each of the second raised teeth consists of a second top edge, a third lateral, and a fourth lateral, in which the third lateral is connected to the fourth lateral by means of the second top edge, a second included angle formed between the third lateral and a major axis direction of the second rod ranges between 85 and 95 degrees; and the second lateral and the fourth lateral are inclines configured to allow relative movement between the first rod and the second rod after the first raised teeth and the second raised teeth engage with each other.

12. The spine correction kit of claim 11, further comprising a plurality of fixing components for fixing the first rod and the first ring member together, for fixing the second rod and the second ring member together, for fixing the first rod and a target spine together, or for fixing the second rod and the target spine together.

13. The spine correction kit of claim 11, further comprising a spring element provided between the first ring member and the second rod, or between the second ring member and the first rod.

14. The spine correction kit of claim 11, further comprising:
a third rod having a fourth zone,
wherein the first rod further has a third zone that is configured to contact the fourth zone.

15. The spine correction kit of claim 11, wherein the first rod has a first cross-section in its major axis direction, and the second rod has a second cross-section in its major axis direction, in which the first cross-section is configured to face the second cross-section.

16. The spine correction kit of claim 15, wherein the first cross-section and the second cross-section are equal in terms of area.

* * * * *